United States Patent
Riordan et al.

(10) Patent No.: US 6,699,993 B1
(45) Date of Patent: Mar. 2, 2004

(54) PROCESS FOR THE PREPARATION OF 2-CYANOPYRIDINES

(75) Inventors: Peter Dominic Riordan, Dunmow (GB); Mehul Rasikchandra Amin, Haverhill (GB); Timothy Harry Jackson, Cambridge (GB)

(73) Assignee: Bayer CropScience GmbH (DE)

( * ) Notice: Subject to any disclaimer, the term of this patent is extended or adjusted under 35 U.S.C. 154(b) by 31 days.

(21) Appl. No.: 10/070,505

(22) PCT Filed: Aug. 30, 2000

(86) PCT No.: PCT/EP00/09148

§ 371 (c)(1),
(2), (4) Date: Oct. 30, 2002

(87) PCT Pub. No.: WO01/17970

PCT Pub. Date: Mar. 15, 2001

(30) Foreign Application Priority Data

Sep. 7, 1999 (GB) .............................................. 9920959

(51) Int. Cl.$^7$ ............................................. C07D 213/57
(52) U.S. Cl. ...................................................... 546/286
(58) Field of Search ......................................... 546/286

(56) References Cited

U.S. PATENT DOCUMENTS 4,367,336 A * 1/1983 Nishiyama et al. ......... 546/286
4,766,219 A    8/1988 Orvik et al.

FOREIGN PATENT DOCUMENTS

EP    00314917    9/1981
WO    92/18487    10/1992

OTHER PUBLICATIONS

Cram and Hammond, "Organic Chemistry", McGraw Hill Book Co., NY (1964) 2nd ed., pp. 565–567.*

A.M. Shestopalov, "Synthesis Based on 2–Aryl–3–aroyl–1,1–dicyanopropanes", *Journal of Organic Chemistry of the USSR*, (English translation), vol. 20, No. 7, 1984, pp. 1382–1401.

S. Yamaguchi, "The Synthesis of Benzofuranquinolines. VI. A New Synthesis of Benzofuro'2–3–c quinoline Derivatives", *Bulletin of the Chemical Society of Japan*, vol. 63, 1990, pp. 952–954.

* cited by examiner

*Primary Examiner*—Patricia L. Morris
(74) *Attorney, Agent, or Firm*—Ostrolenk, Faber, Gerb & Soffen, LLP

(57) ABSTRACT

The invention relates to a process for the preparation of a compound of formula (I):

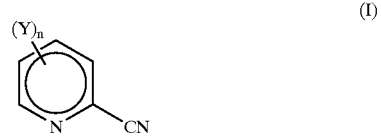

wherein Y and n are as defined in the description.

9 Claims, No Drawings

PROCESS FOR THE PREPARATION OF 2-CYANOPYRIDINES

This invention relates to a novel process for the preparation of 2-cyanopyridines, useful as intermediates for the production of pesticides and pharmaceuticals.

There have been a number of procedures published for introducing a cyano group at the 2-position of a pyridine moiety. These typically involve substitution of a halogen, in particular bromine or fluorine, in a polar solvent, e.g. dimethyl sulfoxide or dimethylformarnmide. In addition, there are numerous methods starting from the activated pyridine N-oxide or N-alkylpyridine. Many of these cyanation routes use heavy metal reagents, containing copper or nickel. For example, EP0034917 discloses the preparation of 2-cyano-3-chloro-5-trifluoromethylpyridine from the 2-bromo analogue by reaction with cuprous cyanide in dimethylfomarnide at 120° C.

However, many of these prior art processes suffer from one or more drawbacks, including poor yields, use of heavy metals which produce toxic effluents, or polar solvents which are difficult to recover. Further, methods which involve formation of the pyridine N-oxide or N-alkylpyridine involve several steps. These drawbacks are more critical on scale-up to industrial scale.

We have now developed an alternative process for the preparation of 2-cyanopyridines which is applicable to industrial scale processes.

According to the present invention there is provided a process for the preparation of a compound of general formula (I):

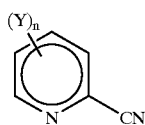
(I)

which comprises treating a compound of general formula (II):

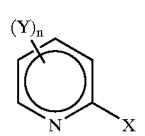
(II)

with an activating agent and a cyanide source in a polar solvent,
wherein
X is halogen;
each Y, which may be the same or different, is an electron withdrawing group; and
n is 1 to 4;
wherein the activating agent is a compound containing a nucleophilic tertiary nitrogen moiety, which activating agent is different from compounds of formnula (I) and (II), and the cyanide source is hydrogen cyanide, an alkali metal cyanide, an alkaline earth metal cyanide or an optionally substituted ammonium cyanide.

Examples of an electron withdrawing group include halogen, haloalkyl, nitro, cyano, alkoxycarbonyl and alkylsulphonyl.

In this invention halogen means a fluorine, chlorine or bromine atom. The preferred halogen atom is chlorine.

Haloalkyl means a C1 to C6 alkyl moiety substituted by one or more halogen atoms. For example the C1 to C6 alkyl moiety may be methyl, ethyl, n-propyl or i-propyl, preferably methyl. The C1 to C6 alkyl moiety is preferably substituted by one or more chlorine or fluorine atoms. A more preferred haloalkyl group is trifluoromethyl.

Preferably Y is halogen or haloalkyl (preferably trifluoromethyl). Preferably X is chlorine.

Compound (II) is preferably 2,3-dichloro-5-trifluoromethylpyridine.

The process of the invention is a high yielding process for the preparation of 2-cyanopyridines, which does not suffer from the drawbacks of many prior art processes. In particular the process of the invention does not require stoichiometric amounts of heavy metal copper or nickel cyanide, which, when used on an industrial scale, produce toxic effluent streams and are difficult to recover. The process of the invention produces waste streams that are readily treatable. In addition, the process does not require the preparation of activated pyridine N-oxide or N-alkylpyridine for high conversions, which is a requisite for many of the prior art processes.

The cyanide source is preferably sodium cyanide or potassium cyanide, especially sodium cyanide. The amount of cyanide source used is generally from about 1.0 to about 2.5 molar equivalents, preferably from 1.4 to 1.6 molar equivalents.

Polar solvents have been found to give the best results. Typical polar solvents which may be used include dimethylformamide, dimethyl sulfoxide, esters such as n-butyl acetate, ethers such as di-n-butyl ether, ketones such as ethyl methyl ketone, and nitriles such as acetonitrile or propionitrile. Acetonitrile and propionitrile are particularly preferred solvents (propionitrile is most preferred). Polar water immiscible solvents are particularly preferred. We have found that in such preferred solvents high conversions do not require anhydrous conditions. Where water soluble cyanides are employed, water may be used as a co-solvent.

The term "nucleophilic tertiary nitrogen moiety" is a moiety containing a nitrogen atom which is not attached to any hydrogen atoms, and which nitrogen is nucleophilic. A variety of tertiary nitrogen nucleophiles can be used as activating agents, especially tertiary amines such as trialkylamines, for example triethylamine; or optionally substituted pyridines, for example 4-pyrrolidinopyridines and especially dialkylarninopyridines, particularly dimethylaminopyridines such as 4-dimethylaminopyridine; or N-alkylimidazoles; or N-alkyltriazoles. 4-Dimethylaminopyridine is the most preferred activating agent.

The amount of activating agent used is generally a stoichiometric amount (generally from 0.9 to 1.5 molar equivalents, preferably from 0.9 to 1.1 molar equivalents), although in some cases a lower quantity (typically from 0.05 to 0.2 molar equivalents) may be sufficient. However when X is chlorine (and especially on larger scales) the use of catalytic amounts of the activating agent generally results in low yields of the compounds of formula (I).

For compounds in which X is fluorine a catalytic amount (typically about 0.15 to about 0.2 molar equivalents) of tertiary nitrogen nucleophile is generally sufficient.

The reaction conditions typically comprise combining all reactants in a suitable reaction vessel and stirring at a temperature of from 20 to 150° C., preferably from 75 to 100° C.

A preferred embodiment of the invention comprises: combining the compound of formula (II), activating agent and polar solvent (preferably propionitrile) in a suitable reaction vessel and stirring at a temperature of about 20 to 150° C., preferably from 75 to 100° C.; followed by (b) treatment of the resulting reaction mixture with aqueous metal cyanide (preferably sodium cyanide) and stirring at about 0 to 90° C., preferably from 20 to 30° C.

A further feature of the invention is that the activating agent may be recycled. This is particularly convenient when using a water immiscible solvent and may be performed by extracting the activating agent from the reaction mixture with dilute aqueous acid, after first taking care to wash out any unreacted metal cyanide with water.

The present invention thus provides a high yielding process for the preparation of 2-cyanopyridines. Since the reaction uses low to moderate reaction temperatures, simple and inexpensive reactors and downstream processing equipment is all that is required. Furthermore, since the activating agent is recycled and because the reactants are readily available, the process is inexpensive to operate. In addition, the present process produces waste streams that are readily treatable.

Prior art processes generally involve displacement of bromine or fluorine by cyanide. These substrates are relatively expensive. Our process proceeds in good yields with the relatively inexpensive chloro-compound. Accordingly, compounds of formula (II) are preferably 2-chloropyridines, especially 2,3-dichloro-5- trifluoromethylpyridine. However, the process also works when X is bromo or fluoro.

The present invention is further illustrated by the following examples. Example 1 shows the effect of varying the reaction conditions on the cyanation of 2,3-dichloro-5-trifluoromethylpyridine as substrate to give 3-chloro-2-cyaro-5-trifluoromethylpyridine. In Table 1 Me means methyl and Et means ethyl. Example 2 shows the effect on conversion of varying the substrate, whilst maintaining constant reaction conditions. Conversions were calculated by GC using a FID (flame ionisation detector).

Example 1

2,3-Dichloro-5-trifluoromethylpyridine (II), the cyanide compound, 4-dimethylaminopyridine (4-DMAP) as activating agent (10% by weight of (II)) and the solvent, were charged into a round bottom flask in the proportions given in Table 1. The reaction conditions are also shown in the table.

TABLE 1

| Expt | Solvent | Catalyst | Cyanide source | Mole ratio of cyanide to II | Reaction conditions | % Conversion |
|---|---|---|---|---|---|---|
| 1 | EtCN | 4-DMAP | NaCN | 1.5 | 98° C. for 10.5 hrs | 92 |
| 2 | MeCN | 4-DMAP | KCN | 1.5 | 84° C. for 10 hrs | 84 |
| 3 | MeCN | 4-DMAP | NaCN | 1.5 | 82° C. for 21 hrs | 75 |
| 4 | Glyme | 4-DMAP | NaCN | 1.5 | 85° C. for 4 hrs | 60 |
| 5 | EtCN | 4-DMAP | Bu₄NCN | 1.0 | 98° C. for 4 hrs | 40 |

Example 2

The compound of general formula (II), propionitrile (4.7 mmols of (II) per 100 ml of propionitrile), sodium cyanide (1.5 mole ratio to compound (II)), 4-dimethylaminopyridine (0.186 mole ratio to compound (II)), water (5% v/v of propionitrile) were charged into a flask and stired at 90–100° C. for 10–12 hours.

TABLE 2

| Expt | Substrate | Reaction Time | Conversion % |
|---|---|---|---|
| 6 | 3-Cl-2-F-CF₃-pyridine | 9 hrs | 92 |
| 7 | 2-Cl-4,5-diCF₃-pyridine | 9 hrs | 49 |
| 8 | 3-Cl2-Br-5-CF₃-pyridine | 10 hrs | 51 |

Example 3

Propionitrile (656 ml), 2,3-dichloro-5-trifluoromethylpyridine (87.5 g) and 4-dimethylaminopyridine (52 g) were heated at reflux for 5 hours under nitrogen. The mixture was cooled and a solution of sodium cyanide (30 g) in water (110 ml) added at 15° C. After stirring at 15° C. for 5 hours the reaction was complete and water (250 ml) added to dissolve the inorganic salts. The organic phase was washed with water followed by extraction with 2N HCl to remove 4-dimethylaminopyridine. Propionitrile was removed by vacuum distillation at 40° C. to give the product, 3-chloro-2-cyano-5-trifluoromethylpyridine in 73 to 84% yield.

Example 4

A reactor was charged with a solution of sodium cyanide (73.5 g) in water (150 ml), propionitrile (500 ml), 4-dimethylaminopyridine (16 g), and 3-chloro-2-fluoro-5-trifluoromethylpyridine (149.3 g) added over 30 minutes. After stirring for 5 hours at 20° C., the upper organic phase was separated off and washed with water. The lower aqueous layer was extracted with propionitrile, the two organic layers combined and solvent distilled off under vacuum at 45° C. to give an 83% yield of 3-chloro-2-cyano-5-trifluoromethylpyridine.

What is claimed is:

1. A process for the preparation of a compound of general formula (I):

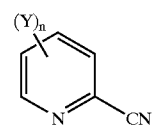

(I)

which process comprises treating a compound of general formula (II):

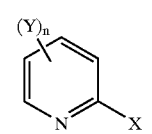

(II)

with an activating agent and a cyanide source in a polar solvent, wherein X is a chlorine or fluorine atom;

each Y, which may be the same or different, is an electron withdrawing group; and n is 1 to 4;

wherein the activating agent is a compound containing a nucleophilic tertiary nitrogen moiety, which activating agent is different from compounds of formula (I) and (II), and the cyanide source is hydrogen cyanide, an alkali metal cyanide, an alkaline earth metal cyanide or an optionally substituted ammonium cyanide.

2. A process according to claim 1 which comprises:

(a) combining the compound of formula (II), activating agent and polar solvent in a suitable reaction vessel and stirring at a temperature of from 75 to 100° C.; followed by treatment of the resulting reaction mixture with aqueous metal cyanide and stirring at 0 to 90° C.

3. A process according to claim 1 in which the activating agent is a tertiary amine selected from trialkylamines, optionally substituted pyridines, N-alkylimidazoles and N-alkyltriazoles.

4. A process according to claim 1 in which the activating agent is 4-dimethylaminopyridine.

5. A process according to claim 1 in which the cyanide source is sodium cyanide or potassium cyanide.

6. A process according to claim 1 in which the polar solvent is acetonitrile or propionitrile.

7. A process according to claim 1 in which the activating agent is recycled.

8. A process according to claim 1 in which X is chlorine.

9. A process according to claim 1 in which the compound of formula (II) is 2,3-dichloro-5-trifluoromethylpyridine.

* * * * *